(12) United States Patent
Martin

(10) Patent No.: US 10,945,884 B2
(45) Date of Patent: Mar. 16, 2021

(54) SYSTEM AND METHOD FOR REDUCING POST-SURGICAL RAINBOW EFFECT

(71) Applicant: Novartis AG, Basel (CH)

(72) Inventor: Peter Martin, Velden (DE)

(73) Assignee: Alcon Inc.

( * ) Notice: Subject to any disclaimer, the term of this patent is extended or adjusted under 35 U.S.C. 154(b) by 35 days.

(21) Appl. No.: 15/117,582

(22) PCT Filed: Oct. 13, 2015

(86) PCT No.: PCT/EP2015/073653
§ 371 (c)(1),
(2) Date: Aug. 9, 2016

(87) PCT Pub. No.: WO2017/063673
PCT Pub. Date: Apr. 20, 2017

(65) Prior Publication Data
US 2018/0207033 A1 Jul. 26, 2018

(51) Int. Cl.
*A61F 9/008* (2006.01)

(52) U.S. Cl.
CPC ...... *A61F 9/00827* (2013.01); *A61F 9/00825* (2013.01); *A61F 2009/00872* (2013.01); *A61F 2009/00897* (2013.01)

(58) Field of Classification Search
CPC ........................ A61F 9/008–2009/0097; A61N 5/06–2005/073
USPC ............................................ 606/4–6, 10–12
See application file for complete search history.

(56) References Cited

U.S. PATENT DOCUMENTS

| | | | | |
|---|---|---|---|---|
| 5,599,340 | A * | 2/1997 | Simon | A61F 9/008 606/4 |
| 8,425,498 | B2 * | 4/2013 | Vogler | A61F 9/008 606/5 |
| 9,078,732 | B2 * | 7/2015 | Dick | A61F 9/00838 |
| 9,918,874 | B2 * | 3/2018 | Dick | A61F 9/008 |
| 10,292,867 | B2 * | 5/2019 | Dick | A61F 9/00838 |
| 2003/0023233 | A1 | 1/2003 | Smith et al. | |
| 2006/0095023 | A1 | 5/2006 | Loesel et al. | |
| 2008/0249513 | A1 * | 10/2008 | Vogler | A61F 9/008 606/5 |
| 2012/0016352 | A1 * | 1/2012 | Dick | A61F 9/00838 606/5 |
| 2015/0297409 | A1 * | 10/2015 | Dick | A61F 9/008 606/5 |

FOREIGN PATENT DOCUMENTS

EP 1977725 A1 10/2008

* cited by examiner

*Primary Examiner* — Jonathan T Kuo

(57) ABSTRACT

The disclosure relates to a pulsed laser system including a laser source that generates a laser beam, a scanner that controls the location of a beam focal point of the laser beam and also the location of a photodisruption formed at the beam focal point in a cornea of an eye, a computer that generates instructions to the laser source and scanner to direct the formation of a regular photodisruption pattern in the cornea, and a noise source that disturbs the location of each photodisruption to cause an irregular photodisruption pattern to form in the cornea, such that diffraction of light by the cornea after formation of the photodisruption pattern is decreased or avoided.

8 Claims, 2 Drawing Sheets

SYSTEM AND METHOD FOR REDUCING POST-SURGICAL RAINBOW EFFECT

CROSS REFERENCE TO RELATED APPLICATIONS

This application is a section 371 national stage phase of International Application No. PCT/EP2015/073653, filed 13 Oct. 2015, titled "SYSTEM AND METHOD FOR REDUCING POST-SURGICAL RAINBOW EFFECT," which is hereby incorporated by reference in its entirety.

TECHNICAL FIELD

The present disclosure relates to a system and method for introducing irregularity into a photodisruption pattern formed in the cornea by a pulsed laser during eye surgery in order to reduce the rainbow effect sometimes seen by patients after the surgery.

BACKGROUND

Refractive eye surgery is commonly used to correct a variety of vision problems. One common such refractive surgery is known as LASIK (laser-assisted in situ keratomileusis) and is used to correct myopia, astigmatism, or more complex refractive errors. Other surgeries may correct corneal defects or other problems. These surgeries may be used alone, but some are also compatible with other vision correction surgeries, such as cataract surgery. For instance, LASIK to correct astigmatism is often combined with cataract surgery.

During LASIK and other refractive eye surgeries, corrective procedures are commonly performed on interior parts of the eye, such as the corneal stroma, rather than on the eye surface. This practice tends to improve surgical outcomes by allowing the corrective procedure to be targeted to the most effective part of the eye, by keeping the outer, protective parts of the eye largely intact, and for other reasons.

The interior part of the eye may be accessed in a variety of manners, but frequently access involves cutting a flap in the cornea. This is particularly true for refractive eye surgeries, such as LASIK, where the corrective procedure is performed on an interior part of the cornea, such as the stroma. The flap allows an outer part of the cornea to be lifted and folded out of the way, permitting access to the interior part of the cornea. In other procedures where a flap is not used, the cornea may nevertheless be cut in some manner to allow access to its interior or to other interior parts of the eye.

The cornea is commonly cut using a pulsed laser, such as a pulsed femtosecond laser, in which the beam focus is moved within the cornea. The pulsed nature of the laser causes it to vaporize corneal tissue in an interspersed pattern, corresponding to the location of the beam focus when the laser is pulsed on, leaving intact corneal tissue corresponding to the location of the beam focus when the laser is off between pulses. Typically the pulsed laser is only on for a very short pulse time, such as a few tens to hundreds of femtoseconds in the case of the femtosecond laser, but it produces a very high power density within a small volume while on, ablating the tissue within that volume. The beam focus then moves to a new location within the cornea before the laser is pulsed on again. This produces a series of small photodisruptions, typically a few micrometers in average size. The small photodisruptions are typically also spaced a few micrometers apart. The interspersed pattern thus formed is such that the corneal tissue is effectively cut, allowing, for instance, the flap to be detached and lifted, while decreasing damage to the corneal tissue by the laser.

As control of the pulsed laser has improved, the interspersed pattern of photodisruptions has become very regular in terms of both average ablation size and ablation spacing. For instance, a highly precise grid pattern is often used to cut the corneal flap during a LASIK procedure. This highly precise grid pattern causes an unintended post-surgical effect in some patients. Specifically, the photodisruptions allow light to be diffracted by the cornea, giving rise to the appearance of a rainbow in the patient's visual. This rainbow effect is most often observed surrounding a sharp edge of an object in the patient's visual field. The rainbow effect may be distracting or otherwise impair vision or it may simply annoy the patient.

Although the rainbow effect is most frequently reported following refractive eye surgery in which a corneal flap is cut, likely due to the extent to the relative large size of the corneal flap it may occur in any refractive or other eye surgery in which a grid pattern is cut in the cornea using a pulsed laser.

SUMMARY

The disclosure relates to a pulsed laser system including a laser source that generates a laser beam, a scanner that controls the location of a beam focal point of the laser beam and also the location of a photodisruption formed at the beam focal point in a cornea of an eye, a computer that generates instructions to the laser source and scanner to direct the formation of a regular photodisruption pattern in the cornea, and a noise source that disturbs the location of each photodisruption to cause an irregular photodisruption pattern to form in the cornea, such that diffraction of light by the cornea after formation of the photodisruption pattern is decreased or avoided.

The pulsed laser system may also include the following elements, which may be combined with one another unless clearly mutually exclusive: i) the laser source may be a femtosecond laser; ii) the scanner may include at least one transverse control element and at least one longitudinal control element; iii) each noise source may be coupled to at least one transverse control element or at least one longitudinal control element, or to multiple control elements; iv) the system may include multiple noise sources, each coupled separately to at least one transverse control element or at least one longitudinal control element; v) the noise source may introduce noise into an electrical signal that controls the location of the photodisruption, such that the location is disturbed, in which case an electrical signal limiter may limit the distance photodisruption is disturbed in any direction; vii) wherein the noise source may physically move an element of the scanner that controls the location of the photodisruption, such that the location is disturbed; viii) the noise source may modify the instructions generated by the computer to direct the formation of a regular photodisruption pattern such that a photodisruption is disturbed, in which case, the noise source may include a pseudo-random number generator or a random number generator, and also in which case the computer may further execute code to check and limit the distance the photodisruption is disturbed; ix) each photodisruption may be disturbed a distance no more than 20% of the spacing between photodisruptions in a given direction in the regular photodisruption pattern; x) the distance each photodisruption is disturbed may be limited such that photodisruptions do not overlap.

The disclosure further includes a surgical suite including any pulsed laser system described above.

The disclosure also includes the use of any pulsed laser system or surgical suite described above to form a cut in the cornea of the eye of a patient undergoing eye surgery, such as refractive eye surgery.

The disclosure further includes a method of performing eye surgery including forming a photodisruption pattern in the cornea of at least one of the patient's eyes to cut the cornea by producing a laser beam with a beam focal point, directing the beam focal point using a scanner to a location in the cornea to cause a photodisruption, and repeating to form a photodisruption pattern, wherein a computer generates instructions for the scanner to form a regular photodisruption pattern, which is disturbed by noise from a noise source, such that diffraction of light by the cornea after formation of the photodisruption pattern is decreased or avoided.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure relates to a system and method for performing eye surgery, such a refractive eye surgery, in which a photodisruption pattern is formed in the cornea of the patient's eye. The system and method introduce irregularity into the photodisruption pattern sufficient to decrease or avoid diffraction of light by the cornea, giving rise to the rainbow effect, after surgery. The system and method introduce this irregularity using a noise source and the scanner of a pulsed laser system, rather than by modifying any parameter of the laser beam source, such as pulse frequency.

Figure 1A:
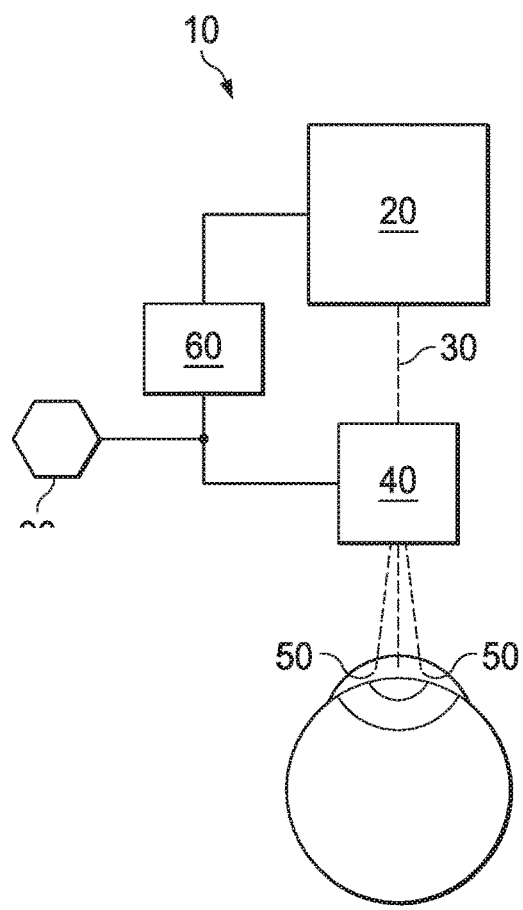
FIG. 1A is a schematic diagram of a pulsed laser system.

FIG. 1A is a schematic diagram of pulsed laser system 10 for use in forming an irregular corneal disruption grid pattern during eye surgery, including refractive eye surgery. Pulsed laser system 10 may be a separate surgical tool, or part of a larger eye surgery system, which may include other laser systems, patient or eye positioning systems, viewing systems, or any combinations thereof. In particular, pulsed laser system 10 may be part of a surgical suite designed to provide substantially all computer-assisted devices for performing a given eye surgery.

Pulsed laser system 10 includes laser source 20, which generates laser beam 30. System 10 includes various components for directing, focusing, or otherwise manipulating laser beam 30, such as scanners, mirrors, beam expanders, and lenses. For simplicity, not all such components are illustrated in FIG. 1A. Scanner 40, however, is illustrated because scanner 40 controls beam focal points 50 located during surgery in the cornea of the patient's eye. Scanner 40 produces an irregular pattern of beam focal points 50, resulting in an irregular photodisruption pattern, such as those illustrated in FIG. 2, FIG. 2B, and FIG. 2C in the cornea of the patient's eye. Laser source 20 and scanner 40 are controlled by computer 60, which may also control other components of pulsed laser system 10. Pulsed laser system 10 may further include housings and other equipment to protect and position its components as well as patient-interface peripherals, which may disposable.

Laser source 20 may include any laser that generates a laser beam 30 in pulses of a selected duration. Laser source 20 may be named according to the pulse duration. For instance, if the pulse duration is in the femtosecond range, such as less than 10 femtoseconds, then laser source 20 is a femtosecond laser.

Figure 2A:
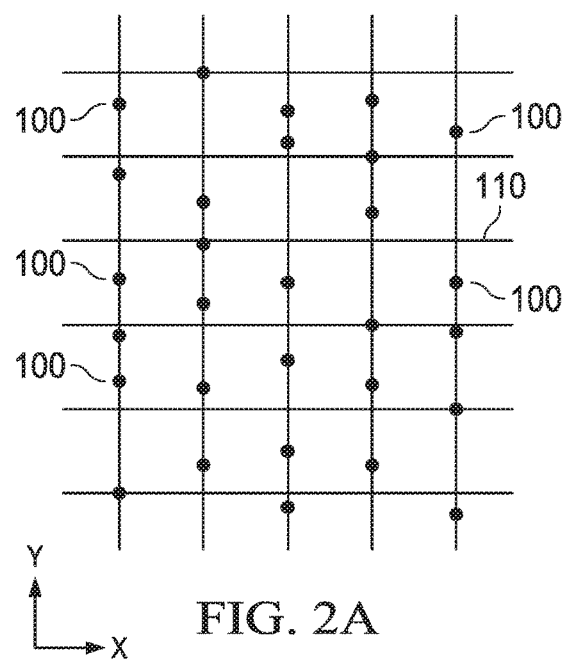
FIG. 2A is a schematic diagram of an irregular photodisruption pattern with disturbances in one dimension.
Figure 2B:
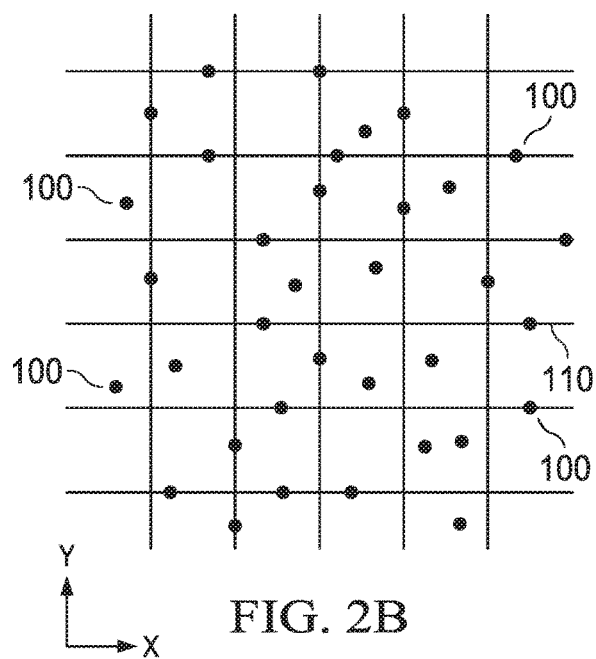
FIG. 2B is a schematic diagram of an irregular photodisruption pattern with disturbances in two dimensions.

Scanner 40 provides transverse and longitudinal control of beam focal points 50. "Transverse" refers to a direction at a right angle to the propagation direction of laser beam 30. A transverse plane is shown in FIG. 2A and FIG. 2B and includes transverse directions x and y. Although the transverse plane may be located anywhere in the cornea of a patient's eye, depending on how the cornea is positioned relative to laser beam 30 when it enters the cornea, typically the transverse plane will be located as depicted in FIG. 2A in FIG. 2B, roughly parallel to the surface of the cornea.

Figure 1B:
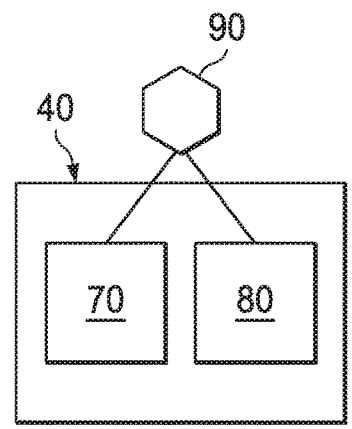
FIG. 1B is a schematic diagram of a scanner in the pulsed laser system of FIG. 1A.
Figure 1C:
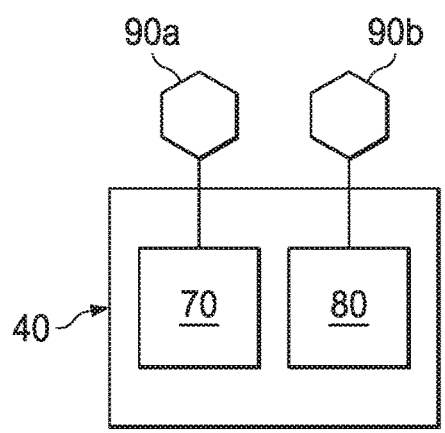
FIG. 1C is a schematic diagram of another scanner in the pulsed laser system of FIG. 1A.

As shown in FIG. 1B and FIG. 1C, scanner 40 may control beam focal points 50 in the transverse plane using a transverse control element 70. Transverse control element 70 may include a pair of mirrors that are tiltable about mutually perpendicular axes. The tilt of these mirrors may be controlled by a galvanometric actuator, piezo motors, a microactuator, or other device. Transverse control element 70 may, alternatively, include an electro-optical crystal.

Figure 2C:
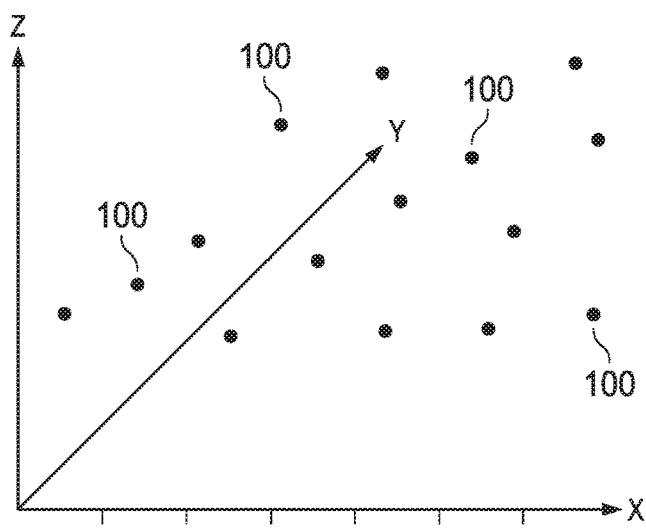
FIG. 2C is a schematic diagram of an irregular photodisruption pattern with disturbances in three dimensions.

"Longitudinal" refers to the propagation direction of laser beam 30. FIG. 2C includes longitudinal direction z. Although the longitudinal direction may also be located anywhere in the cornea of a patient's eye, depending on how the cornea is positioned relative to laser beam 30 when it enters the cornea, typically the longitudinal direction will be located as depicted in FIG. 2C, roughly perpendicular to the surface of the cornea.

Scanner 40 may control beam focal points 50 in a longitudinal direction using a longitudinal control element 80, as shown in FIG. 1B and FIG. 1C. Longitudinal control element 80 may include a longitudinally adjustable lens. Alternatively, longitudinal control element 80 may include a variable refractive power lens. Also alternatively, longitudinal control element 80 may include a deformable mirror.

Scanner 40 may contain more than one transverse control element 70, more than one longitudinal control element 80, or more than one of both. In addition, transverse control element 70 and longitudinal control element 80 may be located in more than one location or device. Similarly, multiple transverse control elements 70 or multiple longitudinal control elements 80 may be in more than one location or device. Scanner 40 may thus include a physically distributed device.

Computer 60 includes at least a processing resource able to execute code to generate instructions to laser source 20 and scanner 40 to form a regular photodisruption pattern in the cornea of a patient's eye. Computer 60 may be in physical or wireless communication with laser source 20 and scanner 40. Computer 60 may further include a memory, particularly a memory for storing instructions for the processing resource, a communications module for communicating with laser source 20 and scanner 40, and other components.

Pulsed laser system 10 further includes a noise source 90 coupled to or located in scanner 40. When computer 60 generates instructions to scanner 40 to locate a beam focal point 50 according to a regular photodisruption pattern, such as photodisruption grid pattern 110 in FIG. 2A and FIG. 2B, noise source 90 disturbs at least one transverse control element 70 or longitudinal control element 80 of scanner 40, such that photodisruption 100 is disturbed from the regular photodisruption pattern. As at least one element is disturbed in connection with multiple instructions generated for multiple beam focal points 50, an irregular photodisruption pattern such as those shown in FIG. 2A, FIG. 2B, and FIG. 2C is produced.

Noise source 90 may include one noise source, or multiple noise sources. One noise source may be coupled to multiple control elements of scanner 40, as shown in FIG. 1B, in which case a similar disturbance is applied to each. Multiple noise sources 90 may each be coupled to a different control element of scanner 40, as shown in FIG. 1C, such that a different disturbance is applied to each.

Noise source 90 may be electrically or physically coupled to one or more control elements of scanner 40 and may include any physical source of a statistically noisy signal, such as thermal noise. Noise source 90 may disturb the control element by introducing noise into an electrical signal received by the element after the signal has left computer 60, if applicable. Noise source 90 may also physically move the control element. When noise source 90 is electrically or physically coupled to one or more control elements of scanner 40, the code executed by computer 60 need not be modified from conventional code that generates a regular photodisruption pattern and computer 60 may simply send instructions for a regular photodisruption pattern. Noise source 90 causes the actual photodisruption pattern to be irregular regardless of the instructions received by scanner 40 from computer 60.

Noise source 90 may also be present in computer 60 any may modify the instructions generated by computer 60 before they are sent to scanner 40. For instance, noise source 90 may be a random or pseudo-random number generator. Noise source 90 may be readily added to conventional code that provides a regular photodisruption pattern by simply causing a modification of the instructions for scanner 40 after they have been generated by the conventional code and before they are sent.

The irregular photodisruption pattern produced using the system and methods of the present disclosure may have disturbances in only one dimension, such as one transverse direction as illustrated in FIG. 2A, or the longitudinal direction (not shown). The disturbances may be in two dimensions, such as in two transverse directions as illustrated in FIG. 2B, or in one transverse direction and the longitudinal direction shown). The disturbances may also be in three dimensions, as illustrated in FIG. 2C.

Typically, each photodisruption 100 has an average dimension of between 2 µm and 5 µm and is a bubble of carbon dioxide and water vapor formed by laser beam 30 at a beam focal point 50.

The distance from which each photodisruption 100 may be disturbed from a regular pattern may be controlled. For instance the distance may be controlled in order to ensure that pulsed laser system 10 actually cuts the cornea, to ensure that the photodisruption does not occur outside of the cornea or in a damaging location, or both. For instance, if noise source 90 is electrically coupled to one or more control elements of scanner 40, when the distance that photodisruption 100 is disturbed may be controlled using an electrical signal limiter, such as a diode. If noise source 90 introduces noise in the instructions sent by computer 60, computer 60 may further execute code to check and limit the distance photodisruption 100 is disturbed.

The distance each photodisruption 100 is disturbed may be no more than a certain percentage of the spacing between photodisruptions in a given direction in the regular photodisruption pattern. For instance it may be no more than 20%, no more than 15%, no more than 10%, or no more than 5% in a given direction. The distance may also be limited such that photodisruptions 100 may not overlap.

Noise source 90, the direction in which it may disturb a photodisruption 100, and any limits on the distance each photodisruption 100 are such that when pulsed laser system 100 is used to form a photodisruption pattern in the cornea during refractive eye surgery or other eye surgery, diffraction of light by the cornea after surgery is decreased or avoided. Thus, the patient experiences no rainbow effect after surgery, or experiences a rainbow effect less often after surgery than if an identical system without noise source 90 were used.

The present disclosure further includes a method of performing eye surgery, such as refractive eye surgery, in which a photodisruption pattern is formed in the cornea of at least one of the patient's eyes to cut the cornea. The method includes using a pulsed laser system, such as system 10, to form the photodisruption pattern. Specifically, a laser source, such as laser source 20, produces a laser beam, such as laser beam 30, which is directed to a beam focal point in the cornea, such as beam focal point 50, by a scanner, such as scanner 40, where it causes a photodisruption, such a photodisruption 100. This process is repeated by pulsing laser source 20 to form a photodisruption pattern in the cornea. The laser source and scanner are controlled by a computer, such as computer 60. Noise is introduced using a noise source, such as noise source 90.

The laser source may produce each laser beam for a time period in the femtosecond range, such as for less than 10 femtoseconds. The time interval between pulses may be in the femtosecond to nanosecond range.

The laser source is controlled by the computer, which executes code on a processing resource and sends instructions to the laser source. The scanner is also controlled by the computer, which executes code on a processing resource and sends instructions to the scanner to cause the beam focal point and photodisruptions to follow a regular pattern, such as that shown in FIG. 2A and FIG. 2B.

The scanner controls the transverse location of the beam focal point using a transverse control element, such as element 70. The transverse location may be controlled and changed by activating at least one of a pair of galvanometric actuators coupled to a pair of mirrors that are tiltable about mutually perpendicular axes. Actuating at least one of the pair of actuators causes the coupled mirror to tilt about its axis. The transverse location may also be controlled and changed by changing the electric field of an electro-optical crystal through which the laser beam passes. The crystal has a change in its refractive index that is linearly proportional to the electric field.

The scanner controls the longitudinal location of the beam focal point using a longitudinal control element, such as element 80. The longitudinal location may be controlled and changed by adjusting a longitudinally adjustable lens, for instance by changing the lens position longitudinally within a housing. The longitudinal location may also be controlled and changed by moving the transverse location of a variable refractive power lens. The longitudinal location may also be controlled and changed by changing the shape of a deformable mirror.

Noise may introduced by coupling an electrical signal or a physical component to a physical noise source, such as a thermal noise source. The noise source may cause a variation in the electrical signal or in the degree of physical movement caused by the physical component. The degree to which the noise disturbs the photodisruption pattern may be controlled by including an electrical signal limiter, such as a diode, between the electrical signal source and any component of the control element that actually positions the laser beam.

Noise may also be introduced by applying a noise source, such as a pseudo-random or random number generator, to the instructions generated by the computer directing a regular photodisruption pattern before the instructions are actually sent to the scanner. The degree to which the noise disturbs the photodisruption pattern may be controlled by further executing code to check and limit the distance photodisruption may be disturbed in any direction.

Thus, an irregular photodisruption pattern in which the photodisruptions are disturbed in one, two or three dimensions is produced. The photodisruptions still effectively produce a cut in the cornea, but they do not diffract light in the cornea, or do not do so as well as a regular photodisruption pattern. As a result, the patient experiences no or fewer rainbow effects after surgery.

This method may be conducted as part of refractive eye surgery, such as LASIK, or any other eye surgery in which the cornea is cut, such as cataract surgery.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A pulsed laser system comprising:
   a laser source configured to generate a laser beam;
   a scanner configured to control the location of a beam focal point of the laser beam and the location of a photodisruption formed at the beam focal point in a cornea of an eye;
   a computer configured to generate instructions to the laser source and the scanner to direct the formation of a regular photodisruption pattern in the cornea; and
   a noise source separate from the computer, the noise source configured to disturb one or more control elements of the scanner to disturb the location of at least one photodisruption to cause an irregular photodisruption pattern to form in the cornea, regardless of the instructions that the scanner receives from the computer that direct the formation of the regular disruption pattern, such that diffraction of light by the cornea after formation of the photodisruption pattern is decreased or avoided, the noise source configured to disturb the one or more control elements by physically moving a control element of the one or more control elements of the scanner, the control element controlling the location of the at least one photodisruption wherein the noise source is a thermal noise source.

2. The pulsed laser system of claim 1, wherein the laser source is a femtosecond laser.

3. The pulsed laser system of claim 1, wherein the scanner comprises at least one transverse control element and at least one longitudinal control element.

4. The pulsed laser system of claim 3, wherein the noise source is coupled to the at least one transverse control element or the at least one longitudinal control element.

5. The pulsed laser system of claim 1, further comprising an electrical signal limiter to limit a distance the photodisruption is disturbed in any direction.

6. The pulsed laser system of claim 1, wherein each photodisruption is disturbed a distance no more than 20% of the spacing between photodisruptions in a given direction in the regular photodisruption pattern.

7. The pulsed laser system of claim 1, wherein a distance each photodisruption is disturbed is limited such that photodisruptions do not overlap.

8. The pulsed laser system of claim 1, wherein the noise source is configured to disturb the one or more control elements of the scanner to disturb the series of locations of the beam focal point in an x, y, and z-dimension.

* * * * *